US012788323B1

(12) United States Patent
Namdeo et al.

(10) Patent No.: US 12,788,323 B1
(45) Date of Patent: Nov. 10, 2026

(54) TUBE-BASED SMART RING WITH REPLACEABLE SENSOR ASSEMBLY

(71) Applicant: ULTRAHUMAN HEALTHCARE PVT LTD, Bangalore South (IN)

(72) Inventors: Yogansh Namdeo, Bangalore South (IN); Anoop Jayan, Bangalore South (IN); Sreeragh Poonthottathil, Bangalore South (IN); Satvik Karkera, Bangalore South (IN); Mainak Mitra, Bangalore South (IN); Daivik Mahamuni, Bangalore South (IN); Akash Raja Puranam, Bangalore South (IN); Atharva Wankhede, Bangalore South (IN); Mohit Kumar, Bangalore South (IN); Vatsal Singhal, Bangalore South (IN)

(73) Assignee: ULTRAHUMAN HEALTHCARE PVT LTD, Bangalore South (IN)

( * ) Notice: Subject to any disclaimer, the term of this patent is extended or adjusted under 35 U.S.C. 154(b) by 0 days.

(21) Appl. No.: 19/344,297

(22) Filed: Sep. 29, 2025

Related U.S. Application Data

(63) Continuation of application No. PCT/IN2025/051206, filed on Aug. 7, 2025.

(30) Foreign Application Priority Data

May 27, 2025 (IN) ............................. 202541050805

(51) Int. Cl.
*A61B 5/00* (2006.01)

(52) U.S. Cl.
CPC .......... *A61B 5/6826* (2013.01); *A61B 5/0002* (2013.01); *A61B 5/0059* (2013.01); *A61B 2562/12* (2013.01); *A61B 2562/166* (2013.01)

(58) Field of Classification Search
CPC ... A61B 5/6826; A61B 5/0002; A61B 5/0059; A61B 2562/12; A61B 2562/166
See application file for complete search history.

(56) References Cited

U.S. PATENT DOCUMENTS

| | | | | |
|---|---|---|---|---|
| 10,496,131 | B2 * | 12/2019 | von Badinski | G06F 1/163 |
| 11,850,069 | B1 * | 12/2023 | Mars | A61B 5/6826 |
| 12,052,816 | B1 * | 7/2024 | Mars | H04W 8/06 |
| 12,436,565 | B2 * | 10/2025 | Chen | G06F 1/163 |
| 2021/0037932 | A1 * | 2/2021 | Min | A61B 5/0006 |

(Continued)

FOREIGN PATENT DOCUMENTS

| | | |
|---|---|---|
| WO | 2024194687 A1 | 9/2024 |
| WO | 2025012856 A1 | 1/2025 |

*Primary Examiner* — Sang H Nguyen
(74) *Attorney, Agent, or Firm* — Renner, Otto, Boisselle & Sklar, LLP

(57) ABSTRACT

A smart ring may include an open arc-shaped tubular housing formed from a metal material and configured to define an internal volume/cavity with an opening. A printed circuit board (PCB) with a sensor assembly may be inserted into the internal volume/cavity through the opening of the housing. A lens may be positioned above the PCB to cover at least a portion of the PCB within the housing. A bottom cover may be manufactured, for example by CNC machining, and may be attached to the opening of the tubular housing to enclose the PCB and the lens, completing body of the smart ring.

7 Claims, 7 Drawing Sheets

(56) References Cited

U.S. PATENT DOCUMENTS

| | | | | |
|---|---|---|---|---|
| 2023/0270384 | A1* | 8/2023 | Apoorv | A61B 5/6826 600/301 |
| 2024/0000204 | A1 | 1/2024 | Doval | |
| 2024/0324957 | A1* | 10/2024 | Realubit | A61B 5/02427 |
| 2025/0009085 | A1* | 1/2025 | Mäkinen | A44C 9/02 |
| 2025/0064396 | A1* | 2/2025 | Järvelä | G16H 40/67 |
| 2025/0071535 | A1* | 2/2025 | Cho | H04W 8/005 |
| 2025/0076982 | A1* | 3/2025 | Kim | A61B 5/1172 |
| 2025/0104464 | A1* | 3/2025 | Jung | G06F 1/163 |
| 2025/0108545 | A1 | 4/2025 | Haverinen | |

* cited by examiner

100

100

TUBE-BASED SMART RING WITH REPLACEABLE SENSOR ASSEMBLY

RELATED APPLICATIONS

This is a bypass continuation of International Application No. PCT/IN2025/051206, filed Aug. 7, 2025, which claims priority to Indian Application No. 202541050805, filed May 27, 2025, each of which is hereby incorporated herewith by reference in their entirety.

FIELD OF INVENTION

The present invention relates to the field of smart wearable devices that incorporate electronic components for functions such as health monitoring, activity tracking, and communication. More specifically, the present invention relates to a smart ring that uses a tube-based structural design.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

Wearable electronic devices have gained significant attention in recent years due to their ability to provide users with convenient features such as health monitoring, activity tracking, notifications, and communication with other connected devices. Smart rings, in particular, have become popular as compact and discreet wearables that can house various sensors and electronic components in a form factor small enough to be worn comfortably on a finger. However, designing a smart ring that is both small and strong, and that protects internal electronics while remaining easy to assemble and maintain, may pose a technical challenge.

Traditionally, smart rings are constructed with solid housings or molded plastic shells that completely enclose the internal electronics. While solid housings can provide basic protection, they often limit overall strength of the ring and can make it difficult to manage heat generated by the internal electronics. Such solid housings also complicate assembly process because internal electronics like a printed circuit board (PCB) and sensors must be inserted and sealed inside ring body, sometimes requiring adhesives or welding. Such insertion increases manufacturing time and cost and can make it impractical to open the ring later for repairs or replacement of internal parts, which can reduce the product's useful life. There is therefore a need for a smart ring structure that provides better strength and durability while remaining lightweight, easy to maintain and comfortable to wear.

SUMMARY OF THE INVENTION

This summary is provided to introduce aspects related to a tube-based smart ring with replaceable sensor assembly, and the aspects are further described below in the detailed description. This summary is not intended to identify essential features of the claimed subject matter, nor is it intended for use in determining or limiting the scope of the claimed subject matter.

In an embodiment of the present disclosure, a smart ring is disclosed. The smart ring comprises an open arc-shaped tubular housing configured to form a portion of body of the smart ring. Further, the smart ring comprises a sensor assembly, on a printed circuit board (PCB), configured to be inserted into opening of the open arc-shaped tubular housing. The smart ring further comprise a lens positioned above the sensor assembly and forms at least a portion of inner perimeter of the smart ring and a bottom cover configured to attach to and cover outer perimeter of the open arc-shaped tubular housing to complete the body of the smart ring, and configured to enclose the sensor assembly and the lens within the open arc-shaped tubular housing.

In an aspect of the present disclosure, the lens comprises at least one of a transparent or a semi-transparent material, configured to allow optical transmission to and from the sensor assembly.

In an aspect of the present disclosure, the sensor assembly includes one or more sensors selected from biometric sensors, temperature sensor, photoplethysmography (PPG) sensor, motion sensors, proximity sensors, bioimpedance sensor, capacitance sensor, vibration motor, heart rate sensor, blood oxygen ($SpO_2$) sensor, electrodermal activity (EDA) sensor, ambient light sensor, galvanic skin response (GSR) sensor, ultraviolet (UV) sensor, and electrocardiogram (ECG) sensor, assembled on or on separate modules affiliated to the PCB.

In an aspect of the present disclosure, the PCB further comprises a communication module configured to wirelessly communicate with an external device.

In an aspect of the present disclosure, the open arc-shaped tubular housing defines an internal volume/cavity dimensioned to securely assemble the PCB in any orientation and position the PCB against movement or vibration during use.

In an aspect of the present disclosure, the bottom cover is removable to allow access to the PCB, battery, the sensor assembly, and the lens for repair, replacement, or maintenance.

In an aspect of the present disclosure, the open arc-shaped tubular housing and the bottom cover are dimensioned to form a continuous external surface when assembled.

In an aspect of the present disclosure, the PCB is flexible.

In an embodiment of the present disclosure, a method for manufacturing a smart ring, comprising shaping a metal tube into an open arc-shaped tubular housing to define an open internal volume/cavity with an opening sized to receive internal components. The method further comprises fabricating a printed circuit board (PCB) with a sensor assembly, dimensioned to fit within the open arc-shaped tubular housing, such that it is fully enclosed within the cavity formed by the arc shaped tube or partially enclosed within the cavity flowing from within the cavity to outside the cavity or flowing from one end of the tube to the other end passing from the outside of the cavity. Further the method comprises producing a lens, sized to cover at least a portion of the PCB when positioned within a gap formed by open end of the open arc-shaped tubular housing. Furthermore, the method comprises manufacturing a bottom cover configured to fit in openings of the open arc-shaped tubular housing. The method comprises inserting the PCB into the opening of the open arc-shaped tubular housing. The method comprises placing the lens above the sensor assembly within the gap of the open arc-shaped tubular housing. Further, the method comprises attaching the bottom cover to the opening of the open arc-shaped tubular housing to enclose the PCB and the lens and to complete outer perimeter of the body of the smart ring.

In an aspect of the present disclosure, the lens comprises at least one of a transparent or a semi-transparent material, configured to allow optical transmission to and from the sensor assembly.

In an aspect of the present disclosure, the sensor assembly includes one or more sensors selected from biometric sensors, temperature sensor, photoplethysmography (PPG) sensor, motion sensors, proximity sensors, bioimpedance sensor, capacitance sensor, vibration motor, heart rate sensor, blood oxygen ($SpO_2$) sensor, electrodermal activity (EDA) sensor, ambient light sensor, galvanic skin response (GSR) sensor, ultraviolet (UV) sensor, and electrocardiogram (ECG) sensor, assembled on or on separate modules affiliated to the PCB.

In an aspect of the present disclosure, the PCB further comprises a communication module configured to wirelessly communicate with an external device.

In an aspect of the present disclosure, the open arc-shaped tubular housing defines an internal volume/cavity dimensioned to securely position the PCB against movement or vibration during use.

In an aspect of the present disclosure, the bottom cover is removable to allow access to the PCB, the sensor assembly, and the lens for repair, replacement, or maintenance.

In an aspect of the present disclosure, the open arc-shaped tubular housing and the bottom cover are dimensioned to form a continuous external surface when assembled.

In an aspect of the present disclosure, inner volume formed by assembly of the open arc-shaped tubular housing, lens, and bottom cover is filled fully or partially with epoxy or similar encapsulation to improve ingress protection.

Other aspects and advantages of the invention will become apparent from the following description, taken in conjunction with the accompanying drawings, illustrating by way of example the principles of the invention.

BRIEF DESCRIPTION OF THE DRAWINGS

The accompanying drawings constitute a part of the description and are used to provide further understanding of the present invention. Such accompanying drawings illustrate the embodiments of the present invention, which are used to describe the principles of the present invention. The embodiments are illustrated by way of example and not by way of limitation in the figures of the accompanying drawings in which like references indicate similar elements. It should be noted that references to “an” or “one” embodiment in this invention are not necessarily to the same embodiment, and they mean at least one. In the drawings.

Figure 1:
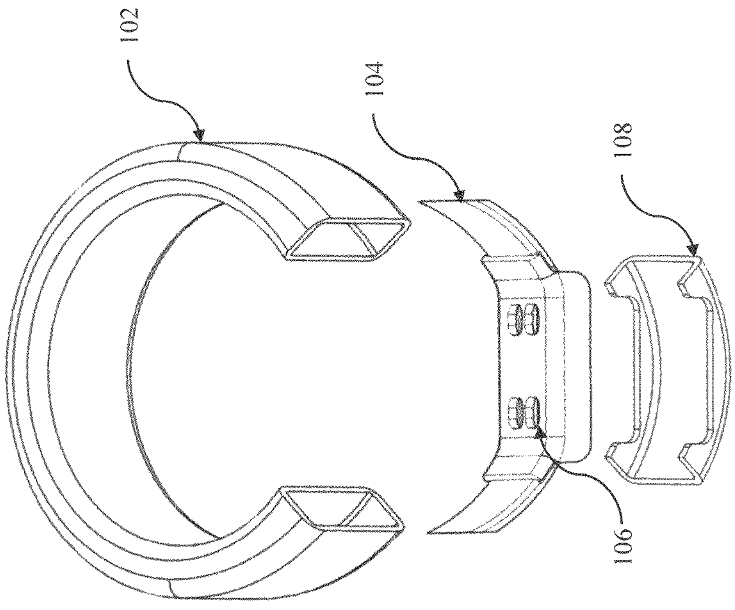
FIG. 1 illustrates an exploded view of a smart ring that uses a tube-based structural design, in accordance with an embodiment of the present invention.

A more complete understanding of the present invention and its embodiments thereof may be acquired by referring to the following description and the accompanying drawings.

DETAILED DESCRIPTION OF THE INVENTION

Exemplary embodiments will now be described with reference to the accompanying drawings. The disclosure may, however, be embodied in many different forms and should not be construed as limited to the embodiments set forth herein; rather, these embodiments are provided so that this disclosure will be thorough and complete, and will fully convey its scope to those skilled in the art. The terminology used in the detailed description of the particular exemplary embodiments illustrated in the accompanying drawings is not intended to be limiting. In the drawings, like numbers refer to like elements.

It is to be noted, however, that the reference numerals used herein illustrate only typical embodiments of the present subject matter, and are therefore not to be considered for limiting its scope, for the subject matter may admit to other equally effective embodiments.

The detailed description includes specific details for the purpose of providing a thorough understanding of the present invention. However, it will be apparent to those skilled in the art that the present invention may be practiced without these specific details.

The present invention addresses structural and integration challenges associated with compact wearable electronics by providing a structure for a smart ring that accommodates modern electronic assemblies. As smart wearables continue to include more features within smaller form factors, there is a demand for configurations that allow sensitive components such as circuit boards, lenses, and connectors to be installed accurately within tight spaces and facilitate easy replacement/maintenance. The smart ring may be manufactured using conventional machining, forming, and assembly operations suited for producing compact metal housings, precision-fit covers, and component alignment features.

The smart ring may comprise four components, namely an open arc-shaped tubular housing, a printed circuit board (PCB), a lens, and a bottom cover. Together, these elements form a compact, modular, and robust wearable device suitable for continuous use on a user’s finger.

Figure 2:
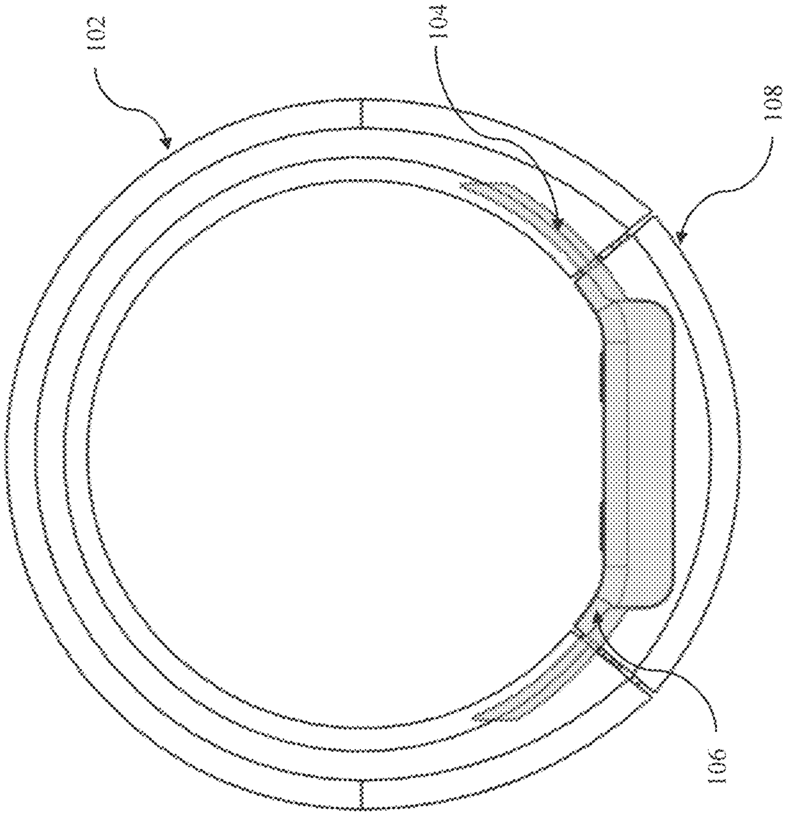
FIG. 2 illustrates an assembled view of the smart ring, in accordance with an embodiment of the present invention.

FIG. 1 and FIG. 2 illustrate an exploded and an assembled view, respectively, of a smart ring 100 that uses a tube-based structural design, in accordance with an embodiment of the present invention. The smart ring 100 may comprise an open arc-shaped tubular housing 102 that may be formed from at least one metal, most preferably a biocompatible including but not limited to, commercially pure titanium (for example, Grade 1) and a titanium alloy. Titanium may provide the smart ring 100 with a high strength-to-weight ratio, resistance to corrosion, and suitability for prolonged skin contact, which are desirable characteristics for wearable electronics. In an embodiment, the open arc-shaped tubular housing 102 may be U-shaped.

In one embodiment, the open arc-shaped tubular housing 102 may be formed from a non-metallic material such as a high-strength polymer, composite material, or ceramic. For example, the housing may be fabricated from an engineering-grade polymer such as polyether ether ketone (PEEK) or polycarbonate to achieve a balance of lightweight structure, durability, and user comfort. In another example, the housing may be formed from a fiber-reinforced composite to provide additional stiffness while maintaining a low profile. In certain embodiments, a ceramic material may be used to provide scratch resistance and a premium surface finish while remaining biocompatible for prolonged skin contact.

The open arc-shaped tubular housing 102 may be hollow and may define an internal volume/cavity that extends along its length. The internal volume/cavity may be dimensioned to securely receive and position a printed circuit board (PCB) within the body of the smart ring 100. In an embodiment, the PCB may be flexible.

The PCB includes a sensor assembly 104. The sensor assembly 104 includes one or more sensors selected from biometric sensors, temperature sensor, photoplethysmography (PPG) sensor, motion sensors, proximity sensors, bio-impedance sensor, capacitance sensor, vibration motor, heart rate sensor, blood oxygen ($SpO_2$) sensor, electrodermal activity (EDA) sensor, ambient light sensor, galvanic skin response (GSR) sensor, ultraviolet (UV) sensor, and electrocardiogram (ECG) sensor, assembled on or on separate modules affiliated to the PCB. Further, the PCB may include a communication module configured for wireless connectivity with external devices such as smartphones, tablets, or computers. As shown in the FIG. 1, the sensor assembly 104 is configured to be inserted through an opening of the open arc-shaped tubular housing 102. The PCB may be dimensioned to slide or press-fit into the internal volume/cavity such that it aligns snugly and remains stable during normal use.

Positioned above the sensor assembly 104 is a lens 106, which is arranged to cover at least a portion of the PCB once seated inside the open arc-shaped tubular housing 102, and forms at least a portion of inner perimeter of the smart ring 100. The lens 106 may be formed of a transparent or semi-transparent material, including but not limited to polycarbonate and hardened glass, and functions as a protective barrier while allowing optical components on the PCB, such LEDs, photodiodes, or display indicators, to interact with the external environment. The lens 106 may be dimensioned to snap-fit with the opening of the open arc-shaped tubular housing 104, contributing to a smooth exterior surface once assembly is complete.

Once the sensor assembly 104 and the lens 106 are positioned within the open arc-shaped tubular housing 102, the opening of the open arc-shaped tubular housing 102 is enclosed using a bottom cover 108. As illustrated in FIG. 1, the bottom cover 108 is configured to attach securely to the open arc-shaped tubular housing 102, enclosing internal components to complete the body of the smart ring. The bottom cover 108 may be formed from a high-grade material, including but not limited to Grade 5 titanium.

The bottom cover 108 may be precisely machined using CNC (Computer Numerical Control) techniques to achieve tight tolerances and a precise fit with the open arc-shaped tubular housing 102. In other embodiments, the bottom cover 108 may be formed using additive manufacturing methods, such as metal 3D printing, direct metal laser sintering (DMLS), selective laser melting (SLM), or binder jetting, which may allow complex internal features or lightweight lattice structures to be incorporated into the cover design. In some embodiments, the bottom cover 108 may be produced using a combination of subtractive and additive manufacturing, such as 3D printing a near-net-shape blank followed by CNC finishing to achieve final tolerances and surface quality. In yet other embodiments, the bottom cover 108 may be fabricated using precision casting, metal injection molding (MIM), or hybrid forming processes, depending on the production scale and desired material properties.

The bottom cover 108 may attach to the open arc-shaped tubular housing 102 by means of a snap-fit design, mechanical tabs, or other suitable interlocking features that provide a secure and stable connection while allowing for disassembly when needed. Modular attachment of the bottom cover and the open arc-shaped tubular housing 102 allows users or technicians to access the PCB and lens 106 for maintenance, upgrades, or replacement without damaging overall structure of the smart ring 100.

In the assembled view shown in FIG. 2, the smart ring 100 is illustrated in its fully enclosed state, with the bottom cover 108 properly engaged to enclose the sensor assembly 104 and lens 106 within the open arc-shaped tubular housing 102. Outer surface of the bottom cover 108 may be dimensioned and shaped to align seamlessly with outer surface of the open arc-shaped tubular housing 102, to form a smooth and continuous external profile, enhancing wearer comfort while protecting internal electronics from dust, moisture, or accidental impact.

Figure 3:
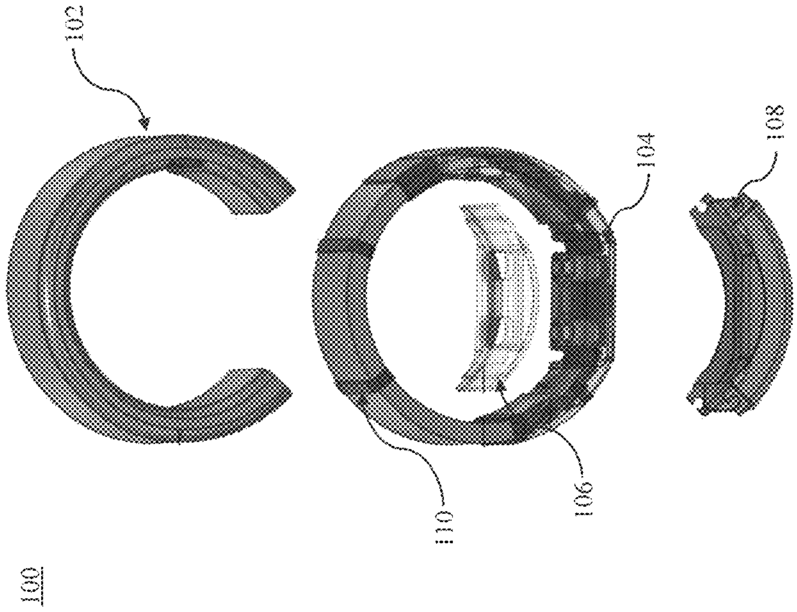
FIG. 3 illustrates exploded 3D view of the smart ring with gaskets, in accordance with another embodiment of the present invention.

Now referring to FIG. 3, an exploded 3D view of the smart ring 100 is illustrated. One or more silicon (Si) gaskets 110 may be circumferentially positioned between inner surface of the open arc-shaped tubular housing 102 and the sensor assembly 104. The Si gasket 110 may function as both a mechanical buffer, absorbing vibrations and minimizing stress on electronic components, and an environmental sealant, restricting ingress of moisture, dust, and particulate contaminants. In some embodiments, the Si gaskets 110 may also be integrated around specific subcomponents such as the battery or sensor chamber to provide localized sealing. Inner volume formed by assembly of the open arc-shaped tubular housing 102, lens 106, and bottom cover 108 is filled fully or partially with epoxy or similar encapsulation to improve ingress protection.

Figure 4:
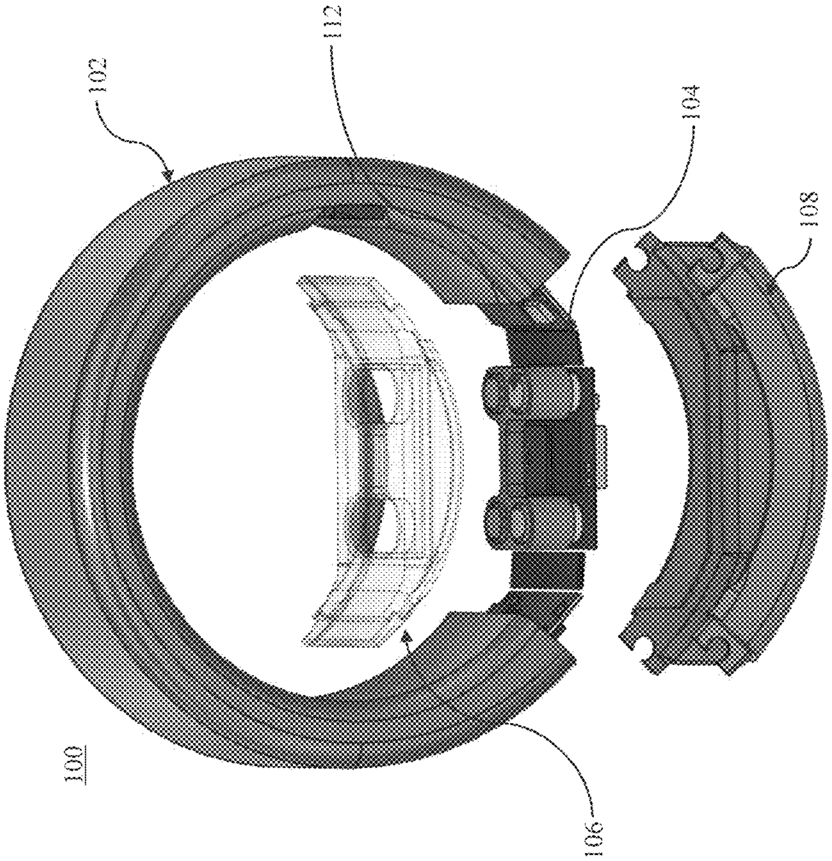
FIG. 4 illustrates an exploded 3D view of the smart ring with a contact pad, in accordance with another embodiment of the present invention.

Referring to FIG. 4, contact pads 112 are disposed on the lower surface of the sensor assembly 104 and are positioned to remain exposed through designated apertures or recesses in the bottom cover 108. The contact pads 112 may serve multiple purposes, including but not limited to, providing electrical connectivity for charging, firmware flashing, diagnostic testing, or data transfer. In one embodiment, the contact pads 112 may be configured to interface with pogo-pin connectors or magnetic charging bases.

To ensure reliable operation, the contact pads 112 may be surrounded by localized gasket structures or over molded insulation barriers that electrically isolate them from adjacent components and prevent fluid ingress.

Figure 5:
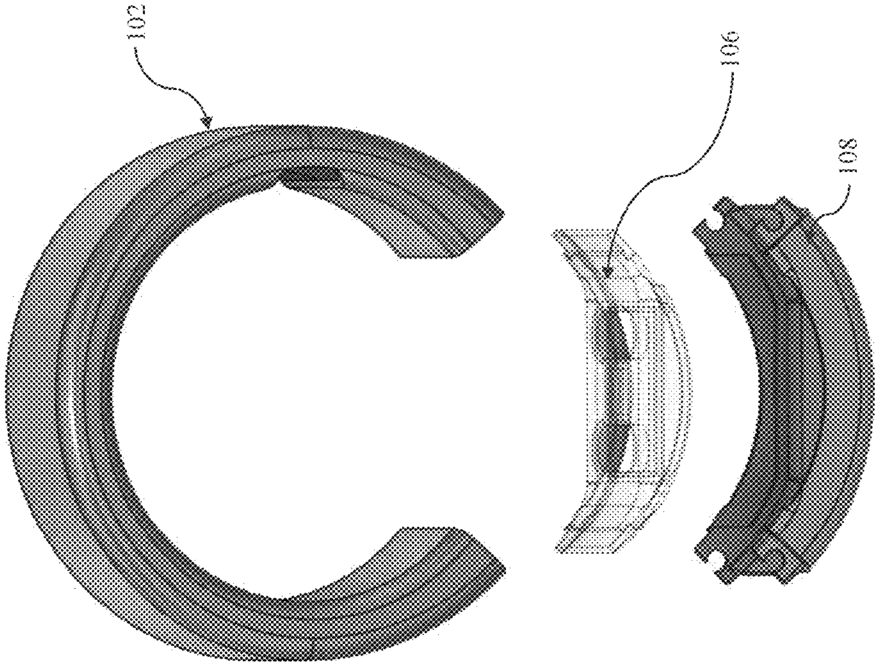
FIG. 5 illustrates an exploded 3D view of the smart ring, in accordance with another embodiment of the present invention.
Figure 6:
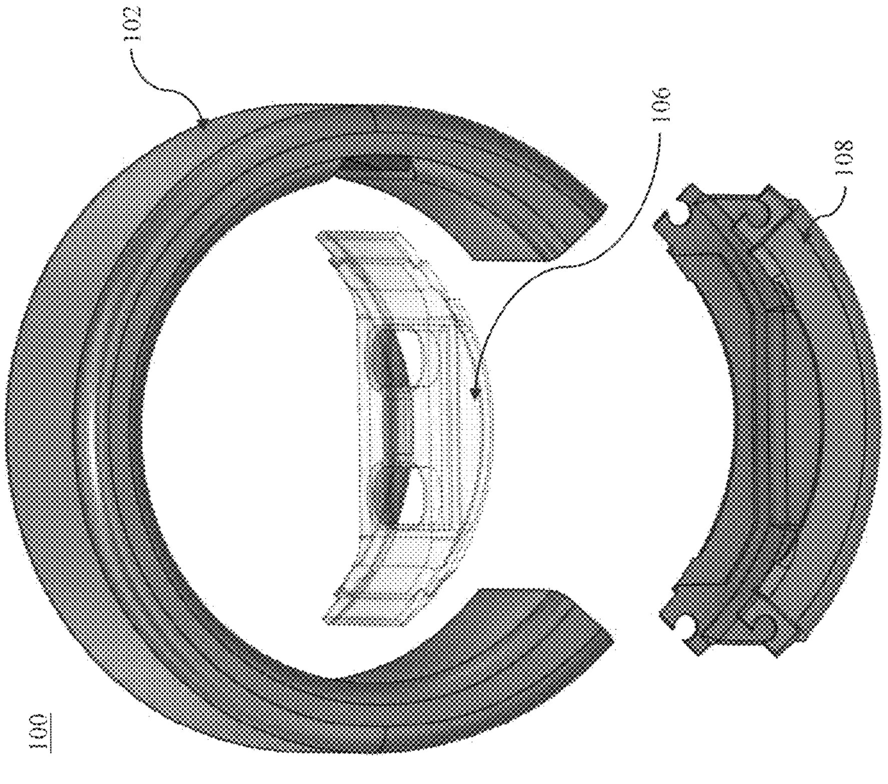
FIG. 6 illustrates an exploded 3D view of the smart ring, in accordance with another embodiment of the present invention.

FIG. 5 and FIG. 6 illustrate an exploded 3D view of the smart ring 100 without the PCB.

Figure 7:
FIG. 7 illustrates a method for manufacturing a smart ring, in accordance with an embodiment of the present invention.

FIG. 7 illustrates a flow chart of a method 700 of manufacturing a smart ring, such as the smart ring 100, in accordance with an embodiment of the present invention. In this regard, each block may represent a module, segment, or portion of code, which includes one or more executable instructions for implementing the specified logical function (s). It should also be noted that in some alternative implementations, the functions noted in the blocks may occur out of the order noted in the drawings.

For example, two blocks shown in succession in FIG. 7 may in fact be executed substantially concurrently or the blocks may sometimes be executed in the reverse order, depending upon the functionality involved. Any process descriptions or blocks in flow charts should be understood as representing modules, segments, or portions of code which include one or more executable instructions for implementing specific logical functions or steps in the process, and alternate implementations are included within the scope of the example embodiments in which functions may be executed out of order from that shown or discussed, including substantially concurrently or in reverse order, depending on the functionality involved. In addition, the process descriptions or blocks in flow charts should be understood as representing decisions made by a hardware structure such as a state machine.

The order in which method is described is not intended to be construed as a limitation, and any number of the described method blocks can be combined in any order to implement the method. Additionally, individual blocks may be deleted from the methods without departing from the scope of the subject matter described herein.

Furthermore, the method can be implemented in any suitable hardware, software, firmware, or combination thereof. Furthermore, the above-mentioned methods may be implemented in suitable hardware, computer-readable instructions, or a combination thereof. The steps of such methods may be performed by either a system under the instruction of machine-executable instructions stored on a non-transitory computer-readable medium or by dedicated hardware circuits, microcontrollers, or logic circuits. The method 700 may include the following steps:

At step 702, a metal tube may be shaped into an open arc-shaped tubular housing to define an open internal volume/cavity with an opening sized to receive internal components.

At step 704, a printed circuit board (PCB), with a sensor assembly, may be fabricated, dimensioned to fit within the open arc-shaped tubular housing, such that it is fully enclosed within the cavity formed by the arc shaped tube or partially enclosed within the cavity flowing from within the cavity to outside the cavity or flowing from one end of the tube to the other end passing from the outside of the cavity.

At step 706, a lens may be produced, sized to cover at least a portion of the PCB when positioned within a gap formed by open end of the open arc-shaped tubular housing. The lens may be formed of a transparent or semi-transparent material, including but not limited to polycarbonate and hardened glass, and functions as a protective barrier while allowing optical components on the PCB.

At step 708, a bottom cover may be manufactured, configured to fit and close the opening of the open arc-shaped tubular housing.

At step 710, the PCB may be inserted into the opening of the open arc-shaped tubular housing.

At step 712, the lens may be placed above the PCB within the opening of the open arc-shaped tubular housing.

At step 714, the bottom cover may be attached to the opening of the open arc-shaped tubular housing to enclose the PCB and the lens and to complete body of the smart ring.

Technical Advancement and Economic Significance

The tube-based smart ring with replaceable sensor assembly disclosed in the present invention may have the following advantages over conventional art:

- Open arc-shaped tubular housing design enables precise internal PCB alignment while maintaining structural integrity in a compact wearable form factor.
- Modular assembly configuration allows simplified insertion, enclosure, and removal of internal components without damaging the housing.
- Use of titanium materials provides high strength-to-weight ratio and biocompatibility for long-term skin contact.
- CNC-machined bottom cover enables high-precision fit and repeatable engagement with the tubular housing, reducing assembly errors.
- Open-channel structure improves manufacturability by avoiding fully enclosed shells that complicate internal access and thermal management.
- Material efficiency and modular construction lower scrap and rework costs during production compared to monolithic ring housings.
- Compact layered design supports integration of advanced sensors and communication modules within minimal physical space.

The specification may refer to “an”, “another”, “one”, or “some” embodiment(s) in several locations.

This does not necessarily imply that each such reference is to the same embodiment(s), or that the feature only applies to a single embodiment. Single features of different embodiments may also be combined to provide other embodiments.

The terms “or” and “and/or” as used herein are to be interpreted as inclusive or meaning any one or any combination. Therefore, “A, B or C” or “A, B and/or C” mean “any of the following: A; B; C; A and B; A and C; B and C; A, B and C.” An exception to this definition will occur only when a combination of elements, functions, steps or acts are in some way inherently mutually exclusive.

As used herein, the singular forms “a”, “an” and “the” are intended to include the plural forms as well, unless expressly stated otherwise. It will be further understood that the terms “includes”, “includes”, “including” and/or “including” when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being “connected” or “coupled” to another element, it can be directly connected or coupled to the other element or intervening elements may be present. Furthermore, “connected” or “coupled” as used herein may include operatively connected or coupled. As used herein, the term “and/or” includes any and all combinations and arrangements of one or more of the associated listed items.

Unless otherwise defined, all terms (including technical and scientific terms) used herein have the same meaning as commonly understood by one of ordinary skills in the art to which this disclosure pertains. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Although implementations of a tube-based smart ring with replaceable sensor assembly have been described in language specific to structural features and/or methods, it is to be understood that the appended claims are not necessarily limited to the specific features or methods described. Rather, the specific features and methods are disclosed as examples of implementations of a tube-based smart ring with replaceable sensor assembly.

The invention has been described above with reference to numerous embodiments and specific examples. Many variations will suggest themselves to those skilled in this art in light of the above-detailed description. All such obvious variations are within the full intended scope of the appended claims.

We claim:

1. A smart ring comprising:

an open arc-shaped tubular housing defining an internal cavity and a gap between two opposing terminal end portions of the open arc-shaped tubular housing in a circumferential direction thereof, the gap defining an opening into the internal cavity of the open arc-shaped tubular housing, the open arc-shaped tubular housing configured to form a portion of a body of the smart ring;

a sensor assembly, on a printed circuit board (PCB), configured to be inserted into the internal cavity through the opening of the open arc-shaped tubular housing;

a lens positioned above the sensor assembly and forming at least a portion of an inner circumference of the smart ring; and a bottom cover configured to attach to the open arc-shaped tubular housing to occupy the gap between the two opposing terminal end portions and cover the opening of the open arc-shaped tubular housing, thereby forming a portion of an outer circumference of the open arc-shaped tubular housing and completing the body of the smart ring, and configured to enclose the sensor assembly and the lens within the open arc-shaped tubular housing, wherein the bottom cover is removable to allow access to the PCB, battery, the sensor assembly, and the lens for repair, replacement, or maintenance.

2. The smart ring as claimed in claim 1, wherein the lens comprises at least one of a transparent or a semi-transparent material, configured to allow optical transmission to and from the sensor assembly.

3. The smart ring as claimed in claim 1, wherein the sensor assembly includes one or more sensors selected from biometric sensors, temperature sensor, photoplethysmography (PPG) sensor, motion sensors, proximity sensors, bioimpedance sensor, capacitance sensor, vibration motor, heart rate sensor, blood oxygen ($SpO_2$) sensor, electrodermal activity (EDA) sensor, ambient light sensor, galvanic skin response (GSR) sensor, ultraviolet (UV) sensor, and electrocardiogram (ECG) sensor, assembled on or on separate modules affiliated to the PCB.

4. The smart ring as claimed in claim 1, wherein the PCB further comprises a communication module configured to wirelessly communicate with an external device.

5. The smart ring as claimed in claim 1, wherein the internal cavity is dimensioned to securely assemble the PCB in any orientation and position the PCB against movement or vibration during use.

6. The smart ring as claimed in claim 1, wherein the open arc-shaped tubular housing and the bottom cover are dimensioned to form a continuous external surface when assembled.

7. The smart ring as claimed in claim 1, wherein the PCB is flexible.

* * * * *